United States Patent
Pattison

[11] Patent Number: 6,010,520
[45] Date of Patent: Jan. 4, 2000

[54] DOUBLE TAPERED ESOPHAGEAL DILATOR

[76] Inventor: C. Phillip Pattison, 470 Navajo West, Lake Quivira, Kans. 66106

[21] Appl. No.: 09/071,576

[22] Filed: May 1, 1998

[51] Int. Cl.⁷ .................................................... A61B 17/00
[52] U.S. Cl. .............................................................. 606/191
[58] Field of Search ..................... 606/190, 191; 604/104, 170, 37

[56] References Cited

U.S. PATENT DOCUMENTS

| | | |
|---|---|---|
| D. 247,512 | 3/1978 | Sandler . |
| D. 265,342 | 7/1982 | Glassman . |
| D. 269,206 | 5/1983 | Glassman . |
| 672,377 | 4/1901 | Kearns . |
| 719,487 | 2/1903 | Minor ...................................... 606/191 |
| 2,763,265 | 9/1956 | Waters ..................................... 606/191 |
| 3,648,683 | 3/1972 | Brodie . |
| 4,449,532 | 5/1984 | Storz . |
| 4,790,314 | 12/1988 | Weaver . |
| 5,109,869 | 5/1992 | Buckley ................................... 606/190 |
| 5,366,471 | 11/1994 | Jones et al. . |

Primary Examiner—Michael Buiz
Assistant Examiner—William Lewis
Attorney, Agent, or Firm—Litman, Kraai & Brown L.L.C.

[57] ABSTRACT

A double tapered esophageal dilator bougie is designed to be disposable after a single use, is radiopaque, and is tapered at both ends to different respective dilator circumferences. Each end of the dilator bougie tapers to two different French sizes available on each end, with one end of the dilator being smaller than the other end. The dilator bougies are produced in graduated sizes and can be packaged as a kit of five. Each bougie in the kit of five is made of a similar PVC material, but the durometer of the PVC decreases as the bougie size increases. This allows each bougie in the kit to have a similar flexibility despite differences in circumference. A central guide wire channel extends the length of each dilator bougie for optional use with a positional guide wire.

19 Claims, 2 Drawing Sheets

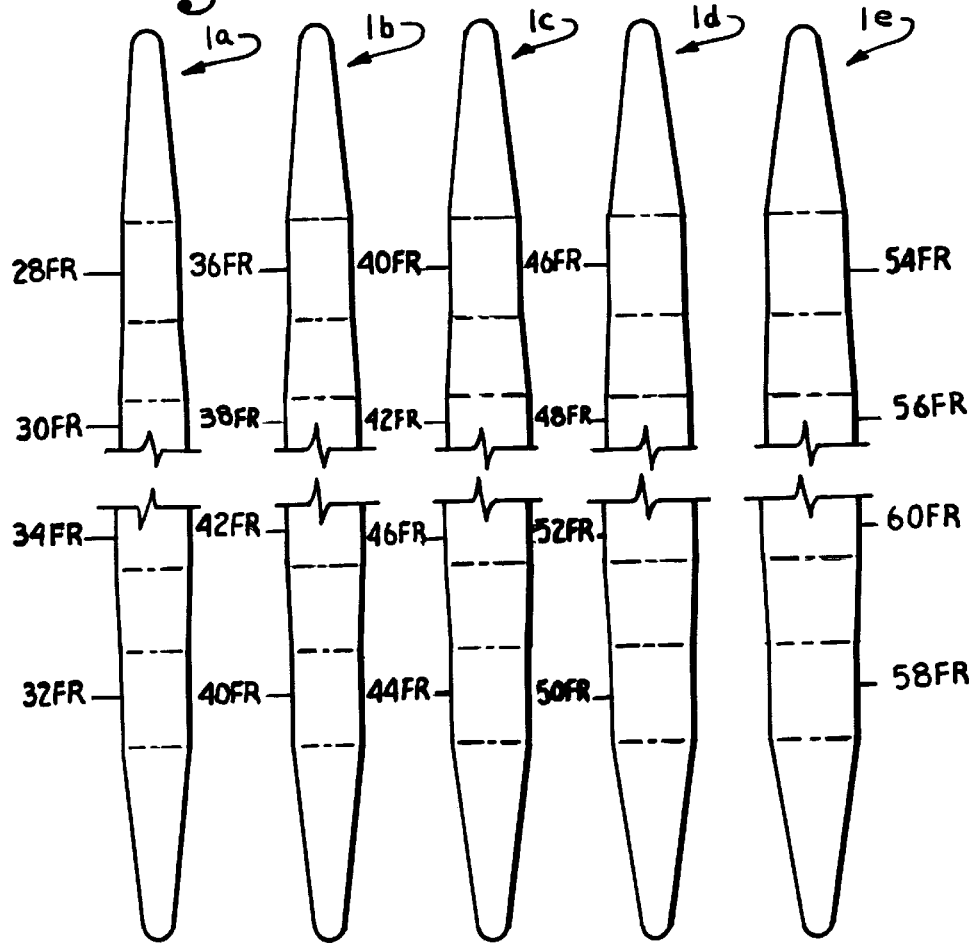
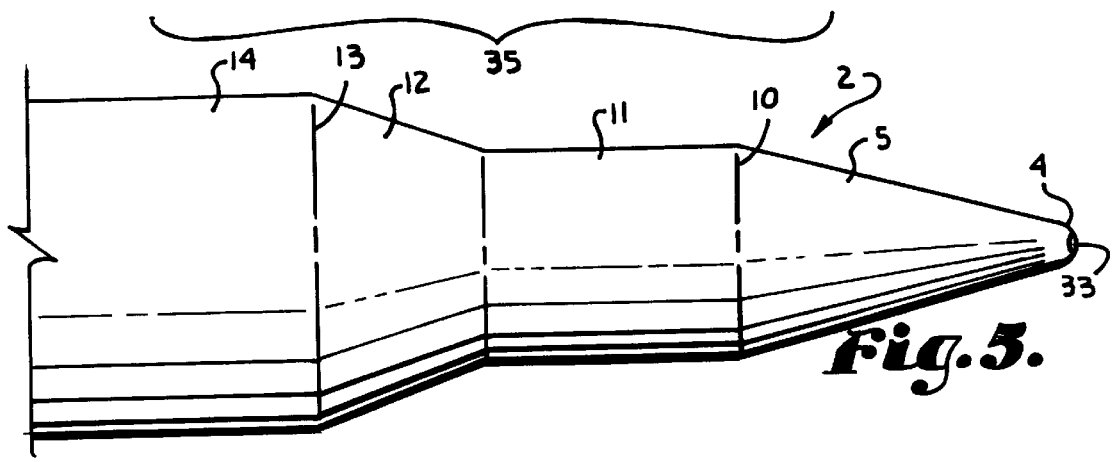

DOUBLE TAPERED ESOPHAGEAL DILATOR

FIELD OF THE INVENTION

The present invention relates to a double tapered esophageal dilator, and, more particularly, to an esophageal dilator which tapers at either end to different respective sizes. The inventive dilator is radiopaque and disposable after a single use and each end is also graduated to two different constant circumferences or "French" sizes.

BACKGROUND OF THE INVENTION

Esophageal strictures in humans can result from a number of causes, both disease and injury related. For example, scar tissue from corrosive injury can cause esophageal stricture, as can cancer, esophagitis, hernia, and cardiospasm, among other causes. These esophageal strictures prevent the normal functioning of the esophagus and can impede a person's ability to swallow and/or block digestive tract access. Treatment for esophageal strictures often involves mechanical dilation by some type of dilator, typically inserted through a patient's mouth.

Mechanical dilators have traditionally fallen into one of three general types. A first type is a tapered "bougie" with a hollow central channel which accommodates a positional guide wire, one end of which has been previously placed in the patent and fed through the esophageal opening. The opposite end of the guide wire is inserted into the central channel of the bougie and the bougie is fed into the patient via the guide wire until the bougie encounters the esophageal stricture. Since the bougie tapers outward, additional pressure on the bougie acts to dilate the stricture. Depending upon the degree of closure, several treatments with increasingly larger bougies may be necessary.

A second type is a balloon dilator which is similarly positional guide wire guided into the patient until the balloon portion of the dilator is positioned in the esophageal opening. The balloon is then slowly inflated, thus putting outward pressure on the esophageal stricture.

Finally, a third category is a Mercury filled bougie, traditionally made of a tapered rubber sheath which is filled with Mercury. The combined flexibility and rigidity achieved by the sheath and the Mercury, as well as the weight of the Mercury allows the bougie to be dropped into position through the patient's mouth and down to the esophageal stricture. Mercury filled bougies have lost favor recently because of the threat of Mercury poisoning from Mercury leaching through cracks in the bougie rubber sheath. Furthermore, Mercury filled bougies can be accidently misdirected into a patient such that they can impact and damage unintended portions of the gastrointestinal tract. In one recently developed dilator, Tungsten particles suspended in a silicone material have been substituted for the Mercury in a bougie, as is taught in U.S. Pat. No. 5,366,471 to Richard G. Jones, et al.

A typical first step of an attending physician with a patient with an esophageal stricture is to insert an endoscope into the esophagal opening in order to estimate the diameter of the stricture. A properly sized dilator is then selected to enlarge the stricture diameter by one or two "French" sizes. A French size is based upon the circumference of the stricture (or dilator) in millimeters.

It is common for all three types of mechanical dilators to include at least some portion which is radiopaque such that they can be used in conjunction with fluoroscopy equipment to accurately locate and diagnose the stricture as well as allowing the attending physician to reliably direct the dilator to the proper place. This prevents the misdirection of the dilator and allows the attending physician to accurately gauge the stricture position.

Prior art mechanical dilators were very expensive due to required exacting manufacturing tolerances, the need to make the bougie at least partially radiopaque and the use of expensive fillers such as Mercury or Tungsten. Due to their high costs, these dilators are typically reused, often for years. This presents serious sterilizing problems, particularly for bougies with hollow central guide wire channels, which are almost impossible to get completely sterile after use. Furthermore, prior art bougies are tapered outward from a tip to a single French size, typically anywhere from 28 to 60 French in circumference. Thus, when multiple dilation insertions with increasingly larger bougies are required, the attendant expense and sterilization problems for each bougie are considerably multiplied. Additionally, each insertion of a different bougie increases throat trauma, and, with guide wire directed dilators, increases the chances of kinking the guide wire within the patient.

An additional problem with prior art dilators is the increasing stiffness of the dilator bougies as size, i.e. working circumference, increases. This makes passage of the bougies through the patient's throat area increasingly more difficult as the size increases since the stiffer bougies do not bend as easily.

It is clear, then, that a need exists for an improved esophageal dilator which avoids the problems attendant in the prior art. Such an improved dilator should preferably be inexpensive enough to be disposable after a single use to avoid sterilization problems, should also minimize the number of insertions required for a dilation treatment, and dilator bougies should be consistent in flexibility over the range of sizes.

SUMMARY OF THE INVENTION

The present invention is a double tapered esophageal dilator which is designed to be disposable after a single use. The inventive esophageal dilator is preferably made of a flexible poly-vinyl chloride (PVC) formulation with Barium sulfate added to render the dilator radiopaque. The dilator is somewhat longer than typical prior art dilators and is tapered at both ends. Each end of the dilator tapers out from a tip to two different French sizes, with one end of the dilator being smaller than the other end. For example, a first end of the dilator may taper out from the tip to a first constant circumference of 28 French, which 28 French circumference extends for about 3 cm along the dilator length. The dilator then tapers outward from the 28 French circumference to a second constant circumference of 30 French which extends along the dilator back to the approximate center thereof. A second, opposite end of the dilator tapers out from the tip to a third constant circumference of 32 French, which 32 French circumference also extends for about 3 cm along the dilator length. The dilator then tapers outward from the 32 French circumference to a fourth constant circumference of 34 French which extends along the dilator back to the approximate center thereof where the dilator circumference transitions between 30 and 34 French. The dilators are produced in graduated sizes from 28–34 French; 36–42 French; 40–46 French; 46–52 French; and 54–60 French and can be packaged as a kit of five. Within the series of dilators, the durometer of the PVC material decreases as the size of the bougies increase, thus resulting in consistency in flexibility throughout the range of bougie sizes. A central guide wire channel extends the length of the dilator for optional use with a positional guide wire.

OBJECTS AND ADVANTAGES OF THE INVENTION

The objects and advantages of the invention include: providing a double tapered esophageal dilator; providing such an esophageal dilator which is disposable after a single use; providing such an esophageal dilator which is tapered at both ends; providing such an esophageal dilator in which a first end tapers outward from a tip to a first and then a second French circumference; providing such an esophageal dilator in which the second end tapers outward from a tip to a third and then a fourth French circumference; providing such an esophageal dilator which is radiopaque; providing such an esophageal dilator with a central guide wire channel for optional guide wire use; providing such an esophageal dilator which can be bundled in kits of five different bougies of incrementally increasing sizes; and providing such an esophageal dilator which is economical to manufacture and which is particularly well suited for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 4 shows a kit containing 5 different esophageal dilator bougies of incrementally increasing sizes, with middle portions of each bougie broken away for ease of illustration.

FIG. 5 is an enlarged, fragmentary end portion of the esophageal dilator bougie of FIG. 1, with the width to length ratio exaggerated to illustrate the two different constant French circumferences and the transitions therebetween.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
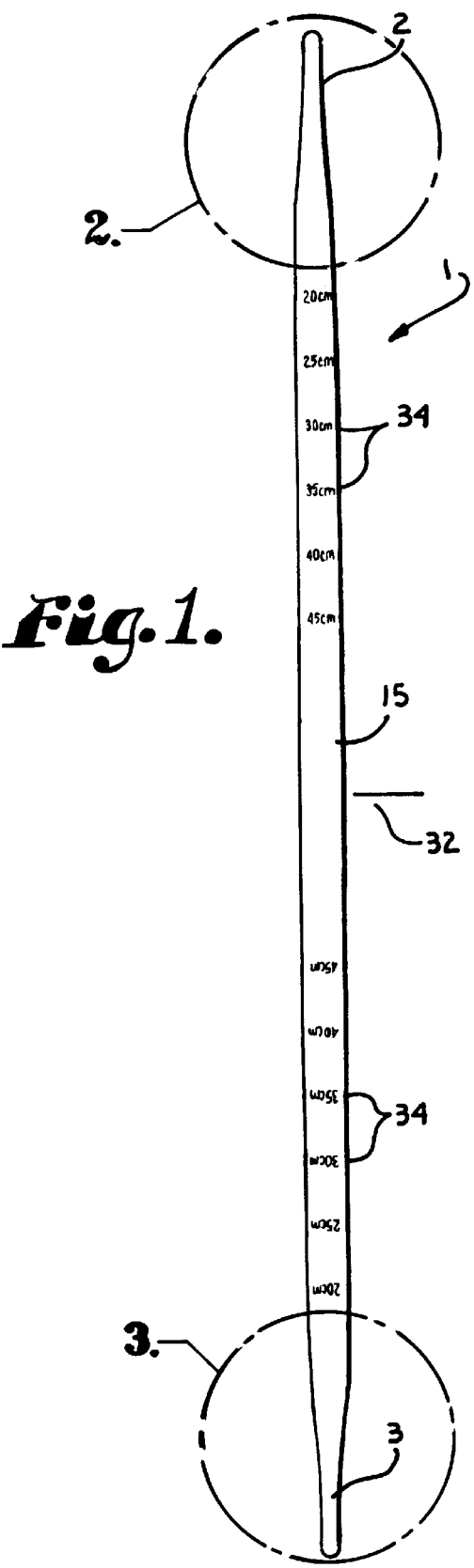
FIG. 1 is a top elevational view of a double tapered esophageal dilator bougie in accordance with the invention.

Referring to the drawings, and particularly FIG. 1, a double tapered esophageal dilator bougie is illustrated and generally indicated at 1. The esophageal dilator bougie 1, which is preferably made of USP Class VI polyvinyl chloride (PVC) which is formulated to include a quantity of Barium Sulfate ($BaSO_4$) which renders the bougie 1 radiopaque throughout its length. The use of these materials yields a bougie 1 which has the desired degree of both rigidity and flexibility required of an ED. At the same time, the bougie 1 is economical enough to manufacture such that it can be used as a one time use—disposable unit.

Figure 2:
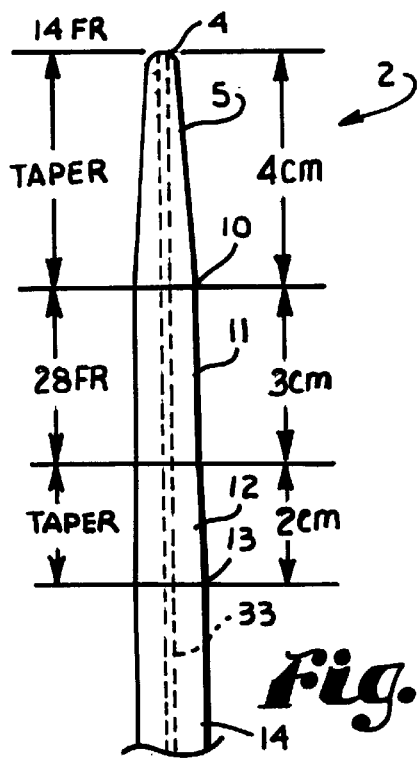
FIG. 2 is a greatly enlarged, fragmentary view of the esophageal dilator of FIG. 1 illustrating the portion of the esophageal dilator which is circled and labeled "2" in FIG. 1.
Figure 3:
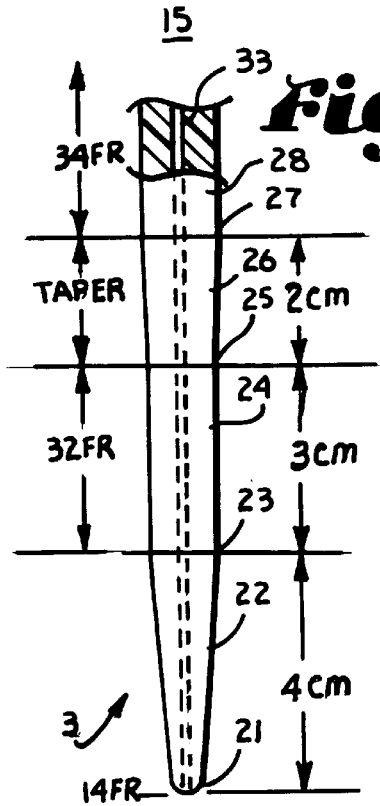
FIG. 3 is a greatly enlarged, fragmentary view of the esophageal dilator of FIG. 1 illustrating the portion of the esophageal dilator which is circled and labeled "3" in FIG. 1, and with portions broken away to illustrate a central guide wire channel.

The esophageal dilator bougie 1 is tapered at a first end 2, as shown in FIGS. 2 and, in exaggerated fashion, in FIG. 5, and at a second end 3, as shown in FIG. 3. The esophageal dilator bougie 1 is somewhat longer than typical prior art dilators, e.g. approximately 210 cm in overall length. The esophageal dilator bougie 1 has two different French sizes available on each of the ends 2 and 3, with the end 2 being smaller in circumference than the end 3. For example, FIGS. 1, 2, 3 and 5 illustrate the smallest available size of bougie 1, with the end 2 tapering outward from a "Maloney" style tip 4 during a length 5 of approximately 4 centimeters to a point 10 where a constant circumference 11 with a dimension of 28 French begins. The tips, such as the tip 4, of each bougie preferably taper downward to a size of approximately 14 French. The circumference 11 of 28 French is constant for a length 5 of approximately 3 cm and the bougie 1 then tapers outward during a length 12 for approximately 2 centimeters to a point 13 where a second constant circumference 14 with a dimension of 30 French begins. The circumference 14 of 30 French is constant from the point 13 backward toward a center portion 15 of the bougie 1.

The end 3, conversely, tapers outward from another Maloney style tip 21 during a length 22 of approximately 4 centimeters to a point 23 where a constant circumference 24 with a dimension of 32 French begins. The circumference 24 of 32 French is constant for a length of approximately 3 cm to a point 25 where the bougie 1 then tapers outward during a length 26 for approximately 2 centimeters to a point 27 where a constant circumference 28 with a dimension of 34 French begins. The circumference 28 of 34 French is constant from the point 13 backward toward a center portion 15 of the bougie 1. In the center portion 15, the bougie 1 transitions between the second and fourth circumferences such that a mid-point 32 of the bougie 1 has a circumference approximately between the two, or about 32 French. FIG. 5 greatly exaggerates the taper between constant circumferences to illustrate the transitions between tapered areas and constant circumferences 12 and 13 of the bougie 1.

FIGS. 2 and 3 illustrate a central guide wire channel 33 which extends the length of the bougie 1. The guide wire channel 33 allows the bougie 1 to be used with an optional positional guide wire (not shown) which has already been fed through a patient's esophagus to accurately guide the bougie into position against any esophageal stricture.

Extending inward from each end 2 and 3 of the bougie 1 are respective series of distance markings 34 beginning at 20 cm and continuing to 45 cm. The measurements to generate these markings 34 are taken either from the point 13 or the point 27, i.e. the beginning point of the innermost constant circumference 14 or 28. The markings 34 give an indication to an attending physician of the depth from a patient's mouth to the innermost constant circumference 14 or 28 being used to dilate that patient's esophageal stricture.

FIG. 4 illustrates five different bougie sizes 1a from 28–34 French, 1b from 36–42 French;, 1c from 40–46 French; 1d from 46–52 French; and 1e from 54–60 French. The five bougies 1a–1e can be packaged as a kit 35 which allows a physician to treat virtually any patient with an esophageal stricture. Although not shown in FIG. 4, each of the bougie sizes 1a–1e also includes a central guide wire channel similar to the channel 33 of FIGS. 2 and 3 which allows the bougies 1a–1e to be used with an optional positional guide wire (not shown). The durometer of the PVC material varies inversely with the size of the bougies. Thus, the bougie 1a has a denser durometer than the bougie 1b, and so on. This results in consistent flexibility of the bougies as the bougie size increases. Thus, unlike prior art esophageal dilators, as bougie size increases, bougie flexibility remains constant, allowing an attending physician to insert each size of bougie with the same ease as the next smaller and the next larger size.

While certain forms of the present invention have been illustrated and described herein, it is not to be limited to the specific forms or arrangement of parts described and shown. For example, the Maloney style tapered tips can be replaced with other conventional tip designs such as "Savary", "Hurst", or "Eder-Puestow". The overall length of the bougie 1 can be adjusted upward or downward from the nominal 210 cm, and the lengths of the constant circumferences 11, 14, 24, 28, etc. and the tapered transition areas 5, 12, 22, and 26 can all be lengthened or shortened as needed for a particular application. A bougie could also incorporate multiple constant circumferences on a single tapered end rather than on each end of a double taper. The French sizes of the kit 35 are exemplary only, and can be adjusted as well, as can the number of bougies in the kit 35. Although PVC material has proven to be an excellent choice, other materials may be suitable and the claims not specifically limited are intended to cover bougies constructed of alternative materials. The markings 34 can be placed more or less frequently than the nominal 5 cm separation illustrated. It is thus to be understood that while certain forms of the present invention have been illustrated and described herein, it is not to be limited to the specific forms or arrangement described and shown.

I claim:

1. An esophageal dilator, comprising:
   a. an elongate bougie made of PVC with a radiopaque compound added thereto with at least one end tapered radially outward from a tip of said bougie and thereafter either remaining constant or increasing in circumference at each point along the length of said bougie end, said one tapered end including:
      i. a first portion which tapers outward from a tip thereof to a first constant circumference;
      ii. said first constant circumference extending in a second portion of said bougie a first predetermined distance along said bougie;
      iii. a third portion which tapers outward from said first constant circumference to a second constant circumference; and
      iv. said second constant circumference extending in a fourth portion of said bougie a second predetermined distance along said bougie.

2. An esophageal dilator as in claim 1, wherein said radiopaque compound is Barium Sulfate.

3. An esophageal dilator as in claim 1, and further comprising a central guide wire channel extending the length of said bougie.

4. An esophageal dilator as in claim 1, and further comprising a plurality of distance markings extending along said bougie to indicate a graduated distance from a beginning point of said second constant circumference.

5. A series of esophageal dilator bougies, each as recited in claim 1, wherein said series of bougies increase in circumference from one bougie to the next and wherein the durometer of the bougie material decreases as bougie size increases.

6. An esophageal dilator, comprising:
   a. an elongate bougie with two ends, each of which are tapered, a first of said tapered ends including:
      i. a first portion which tapers outward from a tip thereof to a first constant circumference;
      ii. said first constant circumference extending in a second portion of said bougie a first predetermined distance along said bougie;
      iii. a third portion which tapers outward from said first constant circumference to a second constant circumference; and
      iv. said second constant circumference extending in a fourth portion of said bougie a second predetermined distance along said bougie;
   b. a second of said tapered ends including:
      i. a fifth portion which tapers outward from a tip thereof to a third constant circumference;
      ii. said third constant circumference extending in a sixth portion of said bougie a third predetermined distance along said bougie;
      iii. a seventh portion which tapers outward from said third constant circumference to a fourth constant circumference; and
      iv. said fourth constant circumference extending in an eighth portion of said bougie a fourth predetermined distance along said bougie.

7. An esophageal dilator as in claim 6, wherein said bougie is made of PVC with a radiopaque compound added thereto.

8. An esophageal dilator as in claim 7, wherein said radiopaque compound is Barium Sulfate.

9. An esophageal dilator as in claim 6, and further comprising a central guide wire channel extending the length of said bougie.

10. An esophageal dilator as in claim 6, and further comprising a plurality of distance markings extending along said bougie to indicate a graduated distance from a beginning point of said second constant circumference.

11. A series of esophageal dilator bougies, each as recited in claim 6, wherein said series of bougies increase in circumference from one bougie to the next and wherein the durometer of the bougie material decreases as bougie size increases.

12. A kit comprising a plurality of esophageal dilators of graduated circumferences, each of said esophageal dilators in said kit comprising:
   a. an elongate bougie with a first tapered end, said first tapered end including:
      i. a first portion which tapers outward from a tip thereof to a first constant circumference;
      ii. said first constant circumference extending in a second portion of said bougie a first predetermined distance along said bougie;
      iii. a third portion which tapers outward from said first constant circumference to a second constant circumference; and
      iv. said second constant circumference extending in a fourth portion of said bougie a second predetermined distance along said bougie.

13. A kit as in claim 12, where in each said esophageal dilator bougie in said kit further comprises:
   a. a second tapered end including:
      i. a fifth portion which tapers outward from a tip thereof to a third constant circumference;

ii. said third constant circumference extending in a sixth portion of said bougie a third predetermined distance along said bougie;

iii. a seventh portion which tapers outward from said third constant circumference to a fourth constant circumference; and iv. said fourth constant circumference extending in an eighth portion of said bougie a fourth predetermined distance along said bougie.

14. A kit as in claim 13, wherein said bougie is made of PVC with a radiopaque compound added thereto.

15. A kit as in claim 13, wherein the PVC comprising said plurality of bougies decreases in durometer as they increase in circumference from one bougie to the next.

16. A kit as in claim 14, wherein said radiopaque compound is Barium Sulfate.

17. A kit as in claim 13, and further comprising a central guide wire channel extending the length of said bougie.

18. A kit as in claim 13, and further comprising a plurality of distance markings extending along said bougie to indicate a graduated distance from a beginning point of said second constant circumference.

19. A kit as in claim 12, wherein the material comprising said plurality of bougies decrease in durometer as they increase in circumference from one bougie to the next.

* * * * *